(12) United States Patent
Segal

(10) Patent No.: US 7,722,656 B1
(45) Date of Patent: May 25, 2010

(54) DEVICE AND METHOD FOR STIMULATING HAIR GROWTH

(76) Inventor: Kim Robin Segal, 5960 W. Parker Rd., #278-227, Plano, TX (US) 75093

( * ) Notice: Subject to any disclaimer, the term of this patent is extended or adjusted under 35 U.S.C. 154(b) by 1065 days.

(21) Appl. No.: 11/363,392

(22) Filed: Feb. 27, 2006

Related U.S. Application Data

(60) Provisional application No. 60/656,256, filed on Feb. 25, 2005.

(51) Int. Cl.
*A61N 5/06* (2006.01)
(52) U.S. Cl. ............... 607/91; 607/88; 607/90
(58) Field of Classification Search ............ 607/88–94; 606/2–19; 128/898
See application file for complete search history.

(56) References Cited

U.S. PATENT DOCUMENTS

| | | | |
|---|---|---|---|
| 5,445,146 A | 8/1995 | Bellinger | |
| 5,616,140 A | 4/1997 | Prescott | |
| 5,755,752 A | 5/1998 | Segal | |
| 5,810,801 A | 9/1998 | Anderson et al. | |
| 5,951,596 A | 9/1999 | Bellinger | |
| 6,033,431 A | 3/2000 | Segal | |
| 6,063,108 A | 5/2000 | Salansky et al. | |
| 6,110,195 A | 8/2000 | Xie et al. | |
| 6,283,956 B1 | 9/2001 | McDaniel | |
| 6,340,233 B1 * | 1/2002 | Shieh | 362/102 |
| 6,450,941 B1 * | 9/2002 | Larsen | 600/14 |
| 6,497,719 B2 | 12/2002 | Pearl et al. | |
| 6,569,156 B1 | 5/2003 | Tankovich et al. | |
| 6,629,971 B2 | 10/2003 | McDaniel | |
| 6,645,230 B2 * | 11/2003 | Whitehurst | 607/88 |
| 6,666,878 B2 * | 12/2003 | Carlgren | 607/91 |
| 6,723,090 B2 | 4/2004 | Altshuler et al. | |
| 6,770,069 B1 | 8/2004 | Hobart et al. | |
| 6,802,853 B1 | 10/2004 | Osendowski | |
| RE38,670 E | 12/2004 | Asah et al. | |
| 2001/0050083 A1 * | 12/2001 | Marchitto et al. | 128/898 |
| 2003/0216797 A1 * | 11/2003 | Oron | 607/89 |
| 2004/0153131 A1 * | 8/2004 | Yorke | 607/91 |
| 2004/0230258 A1 * | 11/2004 | Altshuler et al. | 607/88 |
| 2006/0095099 A1 * | 5/2006 | Shanks et al. | 607/89 |
| 2006/0161226 A1 * | 7/2006 | McMickle | 607/88 |

FOREIGN PATENT DOCUMENTS

JP    2001-070378    *    3/2001

* cited by examiner

*Primary Examiner*—Henry M Johnson, III
*Assistant Examiner*—Aisha Hunte
(74) *Attorney, Agent, or Firm*—James F. Harvey, III

(57) ABSTRACT

The current invention includes a device and method for the promotion and stimulation of hair growth using one or more light sources such as a diode laser, each light source operating in the infrared range at wavelengths in a range from about 2500 nm to about 10,000 nm and at a low wattage, collectively less than about 1000 mw, with the power level typically being in the region of 500 mw. A diode laser operating in this range will have a greater dispersion rate than heretofore, thus requiring fewer diodes to cover the same area of scalp with less power required per diode laser.

14 Claims, 4 Drawing Sheets

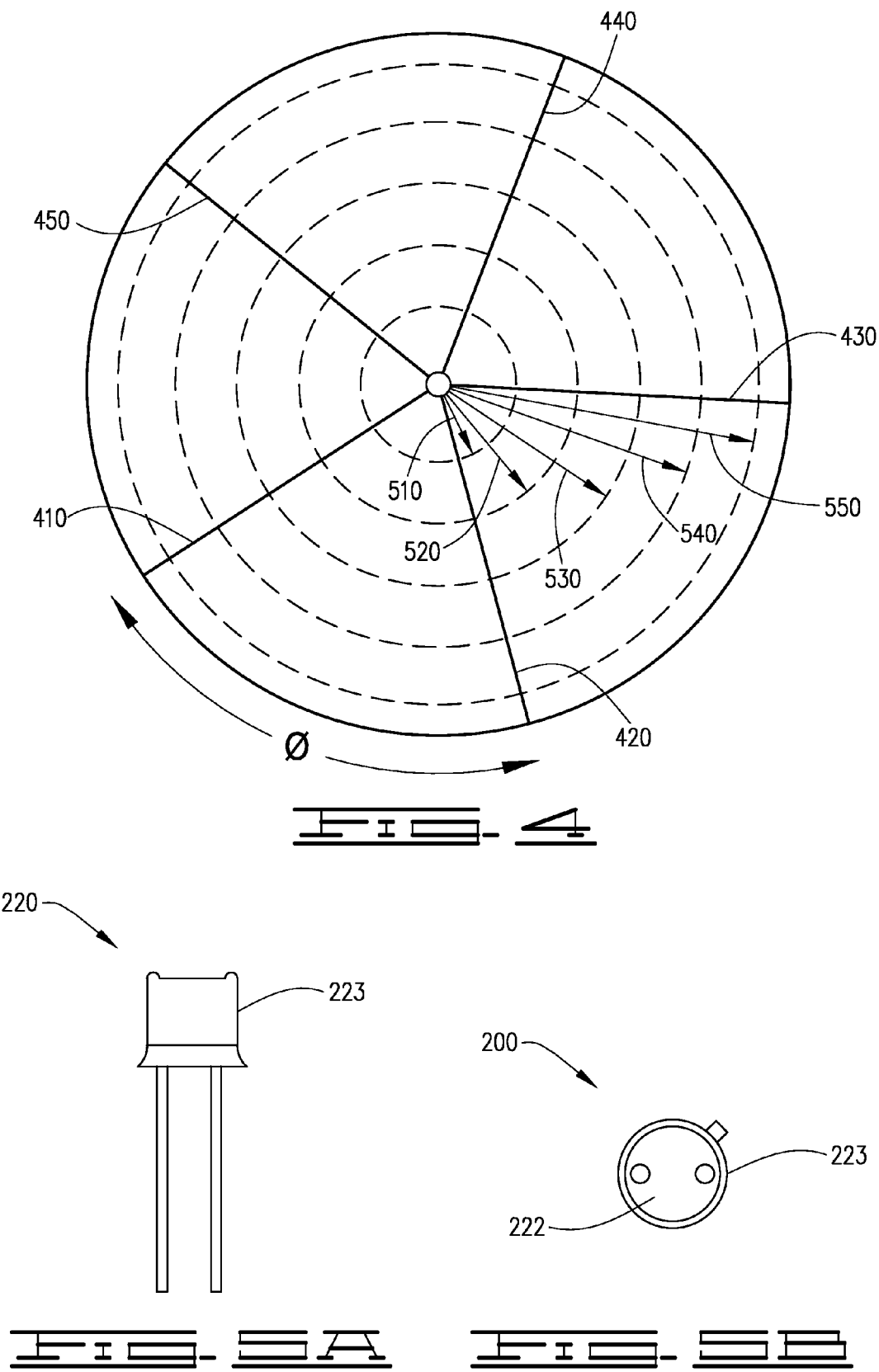

DEVICE AND METHOD FOR STIMULATING HAIR GROWTH

CROSS-REFERENCES TO RELATED APPLICATIONS

This patent application claims the benefit of U.S. Provisional Patent Application No. 60/656,256, filed on Feb. 25, 2005, of same or similar title.

BACKGROUND OF THE INVENTION

This invention generally relates to human hair growth and, more particularly, to methods and devices for stimulating hair growth through stimulation of the hair follicles by means of a laser.

Alopecia (hair loss) is a major concern for the adult population. Expenditures for hair restoration products and treatments for hair loss represent a major component of the multibillion-dollar cosmetic industry in the United States. Examples of techniques for hair retention and regeneration include the use of hair weaving, the use of hairpieces, the application of hair thickening sprays and shampoos, hair transplantation, and the fashioning of coiffures which distribute hair to cover balding regions of the scalp. In addition, topical drug therapies, such as Minoxidil (Rogaine®) or oral drug therapies such as Finasteride (Propecia®), are in current use to stimulate hair growth in men suffering from male pattern baldness, i.e. baldness occurring at the crown and temples. However, this chemical cannot be used by women, can cause a negative skin reaction on the scalp, and is, therefore, not suitable for everyone, and efficacy is limited and not universal.

Diode laser systems have been developed for various medical treatments of the human body. See for example, Applicant's prior U.S. Pat. Nos. 5,755,752 and 6,033,431, which are both incorporated herein by reference in their entirety. Depending on the type of treatment desired, lasers of various wave lengths, periods of exposure and other such influencing factors have been developed.

Lasers are the newest surgical tool for the medical profession because laser light, as a result of its monochromatic and coherent nature, can be selectively absorbed by living tissue. The absorption of the optical energy from laser light depends upon certain characteristics of the wavelength of the light and properties of the irradiated tissue, including reflectivity, absorption coefficient, scattering coefficient, thermal conductivity, and thermal diffusion constant. The reflectivity, absorption coefficient, and scattering coefficient are dependent upon the wavelength of the optical radiation. The absorption coefficient is known to depend upon such factors as interband transition, free electron absorption, grid absorption (photon absorption), and impurity absorption, which are also dependent upon the wavelength of the optical radiation.

In living tissue, the predominant water component has an absorption band determined by the vibration of water molecules. In the visible portion of the spectrum, there exists absorption due to the presence of hemoglobin. Further, the scattering coefficient in living tissue is a dominant factor.

Thus, for a given tissue type, the laser light may propagate substantially unattenuated through the tissue, or may be almost entirely absorbed. The extent to which the tissue is heated and ultimately destroyed depends on the extent to which it absorbs the optical energy and the power associated with the energy. It is generally preferred that the laser light be essentially transmissive through tissues which are not to be affected, and absorbed by tissues which are to be affected. For example, when applying laser radiation to a region of tissue permeated with water or blood, it is desired that the optical energy not be absorbed by the water or blood, thereby permitting the laser energy to be directed specifically to the tissue to be treated. Another advantage of laser treatment is that the optical energy can be delivered to the treatment tissues in a precise, well defined location and at predetermined, limited energy levels.

Ruby and argon lasers are known to emit optical energy in the visible portion of the electromagnetic spectrum, and have been used successfully in the field of opthalmology to reattach retinas to the underlying choroidea and to treat glaucoma by perforating anterior portions of the eye to relieve interocular pressure. The ruby laser energy has a wavelength of 694 nanometers (nm) and is in the red portion of the visible spectrum. The argon laser emits energy at 488 nm and 515 nm and thus appears in the blue-green portion of the visible spectrum. The ruby and argon laser beams are minimally absorbed by water, but are intensely absorbed by blood chromogen hemoglobin. Thus, the ruby and argon laser energy is poorly absorbed by non-pigmented tissue such as the cornea, lens and vitreous humor of the eye, but is absorbed very well by the pigmented retina where it can then exert a thermal effect.

Another type of laser which has been adapted for surgical use is the carbon dioxide ($CO_2$) gas laser which emits an optical beam that is well absorbed by water. The wavelength of the $CO_2$ laser is 10,600 nm and therefore lies in the invisible, far infrared region of the electromagnetic spectrum. It is absorbed independently of tissue color by all soft tissues having a high water content. Since it is completely absorbed, the $CO_2$ laser makes an excellent surgical scalpel and vaporizer since its depth of penetration is shallow and can be precisely controlled with respect to the surface of the tissue being treated.

Another laser in widespread use is the neodymium doped yttrium-aluminum-garnet (Nd:YAG) laser. The Nd:YAG laser has a predominant mode of operation at a wavelength of 1064 nm in the near infrared region of the electromagnetic spectrum. The Nd:YAG optical emission is absorbed to a greater extent by blood than by water making it useful for coagulating large, bleeding vessels. The Nd:YAG laser has been transmitted through endoscopes for treatment of a variety of gastrointestinal bleeding lesions, such as esophageal varices, peptic ulcers, and arteriovenous anomalies.

The foregoing applications of laser energy are thus well-suited for use as a surgical scalpel and in situations where high energy thermal effects are desired, such as tissue vaporization, tissue cauterization, and coagulation.

Although the foregoing laser systems perform well, they commonly generate large quantities of heat and require a number of lenses and mirrors to properly direct the laser light and, accordingly, are relatively large, unwieldy, and expensive. As such, they are unsuitable for use in stimulating hair growth.

Lasers are in increasing use to effect hair removal. This is done by overheating the hair follicles to destroy them. Recently, laser treatment has now been developed specifically for use as a positive stimulating agent for hair growth. The alleged key is to use low power lasers, so as not to destroy, but stimulate the follicles. Several patents have addressed this solution in different way. For example, see U.S. Pat. Nos. 6,497,719, 6,666,878, and 6,802,853. A commercial system similar to that disclosed in the '878 patent uses an array of circumferentially-spaced parallel rows of laser diodes in a hair-dryer type apparatus which rotates. These diodes are carefully arrayed in adjacent rows of staggered diodes to assure overlapping of the light fields of adjacent diodes. The prescribed diodes have a wave length of 400 to 1300 nm (670 nm preferred) and a power sufficient to generate a power density of 7-8 joules/cm². The various embodiments require dozens or even hundreds of diodes. These commercial units are quite expensive and retail for $25,000-$30,000, which severely limits its market and consequent availability to the public for hair growth treatment.

As can be seen, there is a need for a simpler and lower cost system and method for stimulating hair growth with laser energy without damaging the tissue from the thermal effects of the laser energy.

SUMMARY OF THE INVENTION

A method is provided for promoting the hair growth on the head of a patient, where the method comprises the steps of arranging one or more diodes in fixed spacing about the scalp of the patient and at a distance between the diode and the scalp, with each diode emitting a wavelength of coherent light at a specified power level, the wavelength in a range from about 2,500 nm to about 10,000 nm; and moving the fixed spacing of diodes along the scalp according to a periodic cycle within a length of time. This method is accomplished such that a selected portion of the scalp is traversed by the dispersion pattern of a diode at least once during the periodic cycle.

A device is also provided for stimulating hair follicles of a scalp of person through exposure to coherent light, where the device comprises a cap positioned a distance away from and over the scalp, with the cap having one or more light sources arranged to emit a beam of coherent light in a direction of the scalp, the beam having a wavelength in a range of from about 2,500 nm to about 10,000 nm; a means for supporting the cap for rotational movement about the scalp; and a means for controlling the rotational movement of the cap and the actuation of the light sources.

These and other features, aspects, and advantages of the present invention will become better understood with reference to the following drawings, description, and claims.

BRIEF DESCRIPTION OF THE DRAWINGS

FIG. 4 shows a plan plot illustrating another form of laser placement for a bonnet; according to an embodiment of the invention;

FIG. 5A shows a side view of a typical laser diode that can be used to supply coherent light, according to an embodiment of the invention; and FIG. 5B shows a bottom view of a typical laser diode, according to an embodiment of the invention.

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

It is known in a commercially-available hair growth stimulation device to provide laser diodes having a wavelength of about 670 nm, activated at an undisclosed wattage. Applicant's prior patents disclose the use of a laser having wavelengths of from about 1,064 nm to about 2,500 nm for medical treatments that do not involve hair growth stimulation.

Broadly, the current invention includes systems, devices, and methods for a light source, typically a diode laser, operating in the infrared range at wavelengths of greater than about 2,500 nm and at a low total wattage, preferably less than about 1,000 mw for the total output of the device, and more preferably less than about 500 mw. A laser operating in this range will have a greater dispersion rate than heretofore, thus requiring fewer diodes to cover the same area of scalp stimulation for promoting hair growth. A number of factors govern effective scalp stimulation: laser diode wavelength and power (diode wattage); light beam divergence and dispersion; duration period of laser light application/stimulation; rate of application, i.e. the number of periods per unit of time; and the distance between the diodes and the scalp. While prior art devices provide a substantial space between the diodes and the scalp, the Applicant has found that a minimal spacing may be more effective when using diodes in this infrared range and at low wattage.

Figure 1:
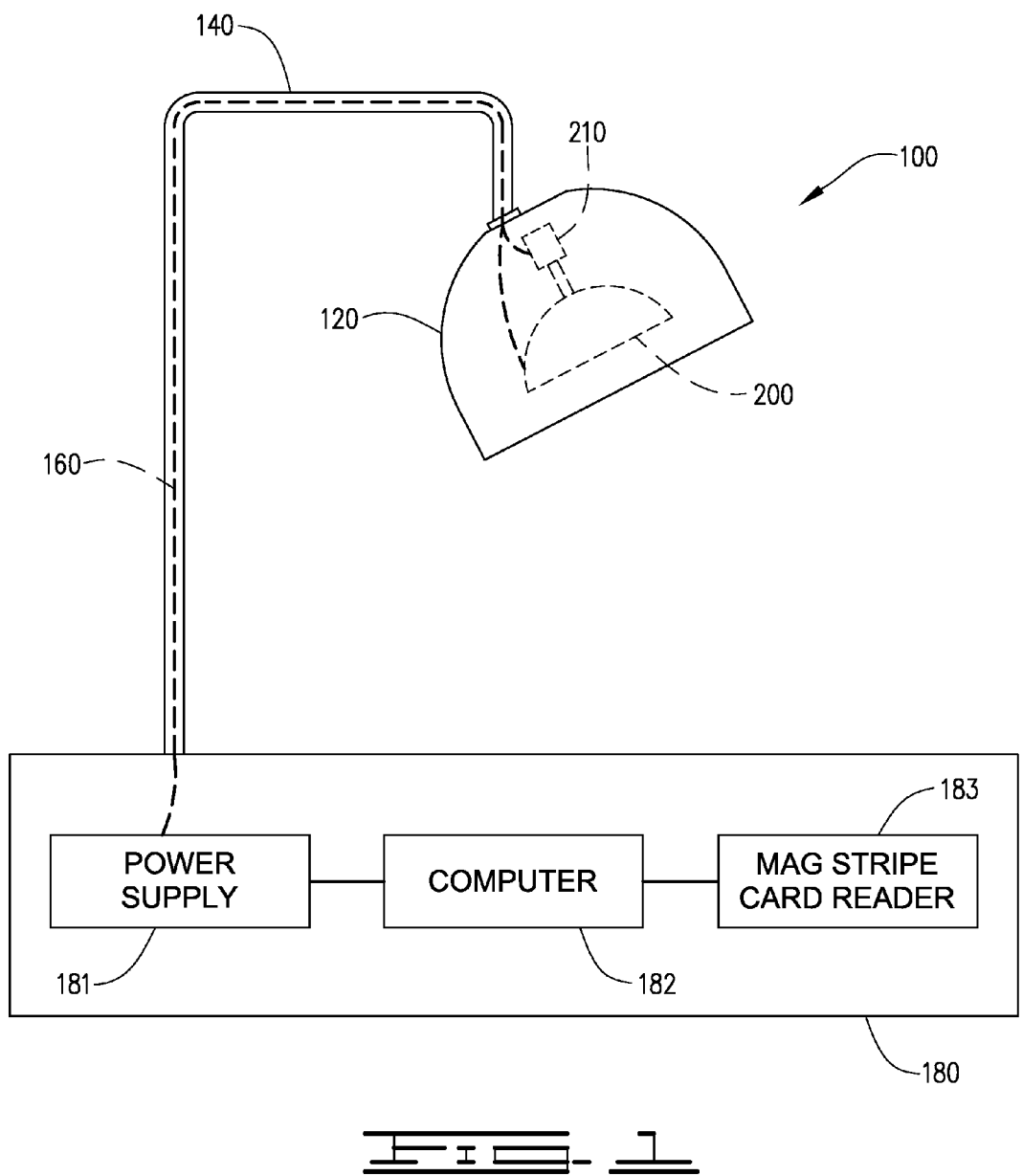
FIG. 1 shows a block diagram of a device for treating patients for hair growth stimulation, according to an embodiment of the invention.

Referring now to FIG. 1, a hair growth stimulation device 100 is shown, which comprises a stationary bonnet 120 provided for surrounding and covering a patient's head, in a manner resembling a well-known hair dryer. Bonnet 120 may be supported on a cantilevered support 140 to allow the bonnet 120 to be positioned over and about the head of a patient while maintaining a non-contact spacing between the interior of the bonnet 120 and the scalp. The patient's head may optionally be supported by an external chair having a neck rest (not shown) so that spacing between the scalp and the interior of the bonnet 120 may be maintained. The bonnet 120 may provide stable support for a cap 200 therein, with the cap 200 being actuated for rotation by a motor 210.

A wiring harness 160 may be provided between the bonnet 120 and a controller 180 that provides control and power to components contained within the bonnet 120. In the embodiment shown, the wiring harness 160 may be routed through a hollow interior of the cantilevered support 140 for convenience and to protect the wiring harness 160 from snagging or damage. However, the wiring harness 160 may also be attached directly to the bonnet 120 by means of a coiled cable, a bundle of bound wires, or other means well known to the art.

The controller 180 may include a power supply 181, a computer 182, an optional magnetic stripe card reader 183, and manual controls (not shown). The power supply 181 may be of standard design having sufficient capacity to power a computer 182, actuate the motor 210 within the bonnet 120 and to drive light sources within the cap 200, as will be described presently. The computer 182 may provide control to the motor and light sources and receive direction from manual controls (not shown) associated with the controller 180. The magnetic stripe card reader 183 may be representative of various input devices well known to the art, which allow data to be provided to and received by the computer 182.

It should be understood that the configuration described above is representative of the inventive device and obvious modifications providing the same functionality may be used within the scope of the invention. For example, in some embodiments, the wiring harness 160 may be replaced by a wireless protocol in which the controller 180 may broadcast control information to a receiving unit located in the bonnet 120, with the controller 180 and the bonnet 120 having their own independent power supplies 181. The magnetic stripe card reader 183 may be substituted with a flash memory card or a floppy disk reader. Other obvious modifications may be contemplated as being within the scope of the invention.

Figure 2A:
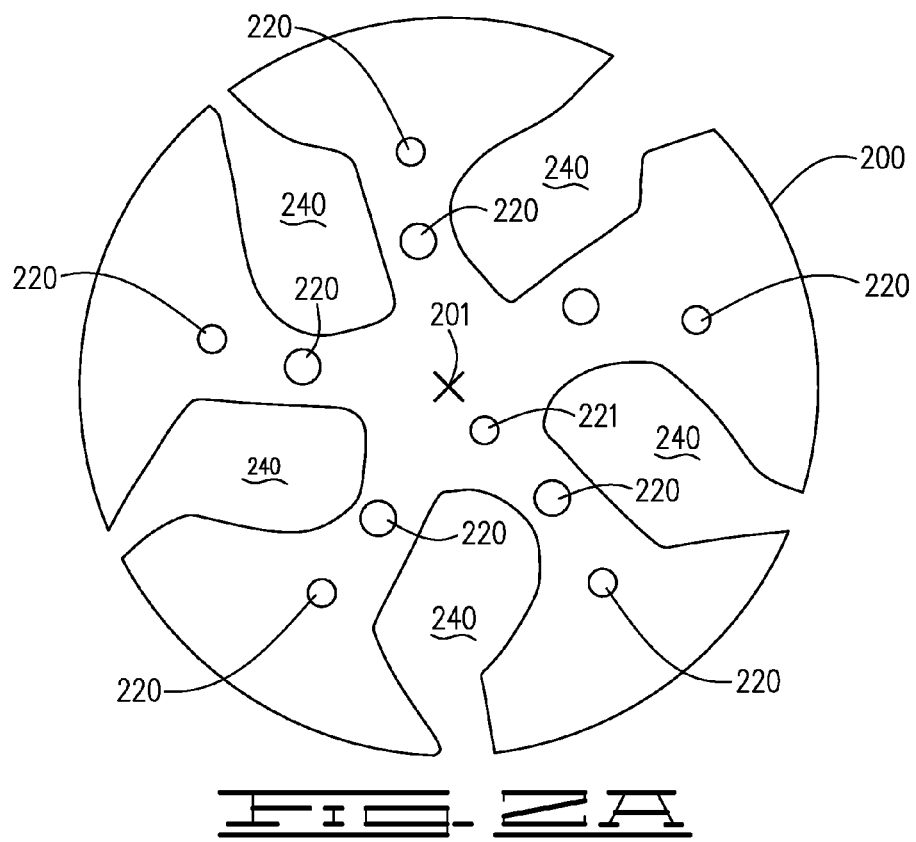
FIG. 2A shows a development view of one form of cap showing the placement of the lasers for one representative embodiment, according to embodiments of the invention.
Figure 2B:
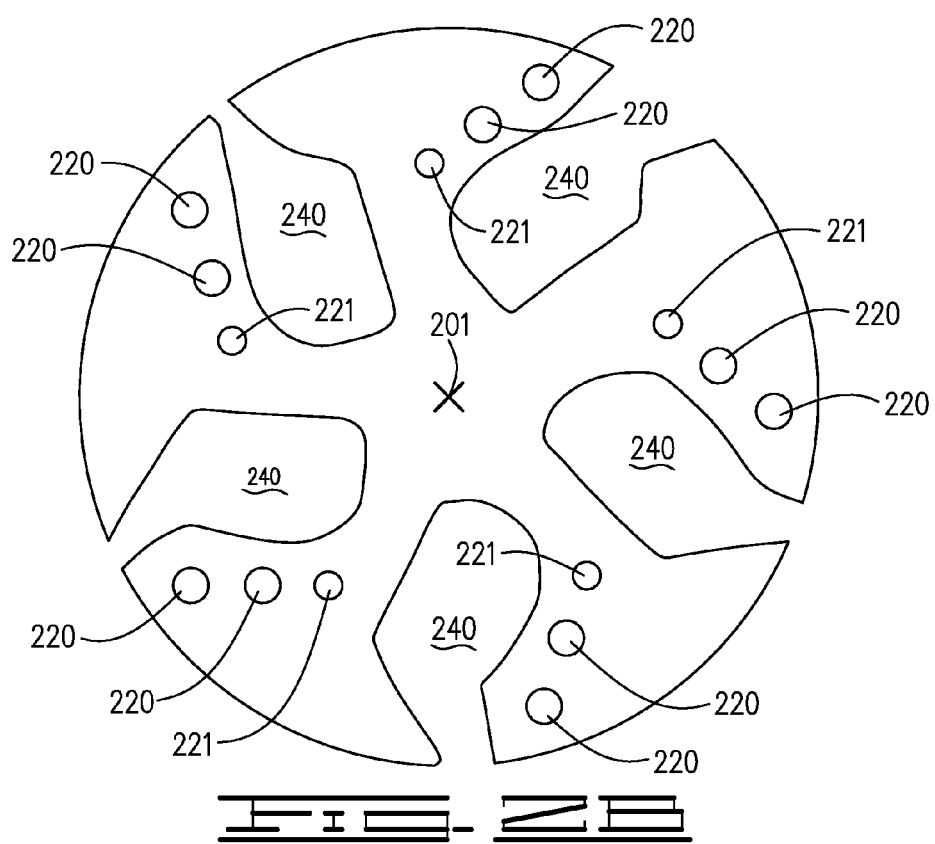
FIG. 2B shows a development view of another form of cap illustrating the placement of the lasers for another representative embodiment, according to embodiments of the invention.

The cap 200 contained within the bonnet 120 may be of a generally circular aspect. A flattened pattern for the cap 200 is shown in FIG. 2, which has a center of rotation 201. Cutouts 240 may be removed from the flattened pattern to allow the resulting shape to assume a three-dimensional form as by bending or folding the portions remaining between the cutouts 240. The cap 200 may be formed by folding each portion inwardly in the same direction to form what geometrically is known as a spherical cap (FIG. 3), which is defined as the shape resulting from a plane passing through a sphere. The diodes 220 in the cap 200 may be inwardly directed towards the interior of the cap 200. The cap 200 thus formed may be sized to allow its shape to be fitted over and around the patient's head for rotational movement without making firm contact with the patient's head. The spherical cap may extend so far as to form a geometric hemisphere, but preferably the spherical cap forming cap 200 may typically comprise from one-half to one-third of a hemisphere. Cap 200 may be fabricated of a thin, durable flexible material, which can be formed into the spherical cap shape as shown in FIG. 3.

Figure 3:
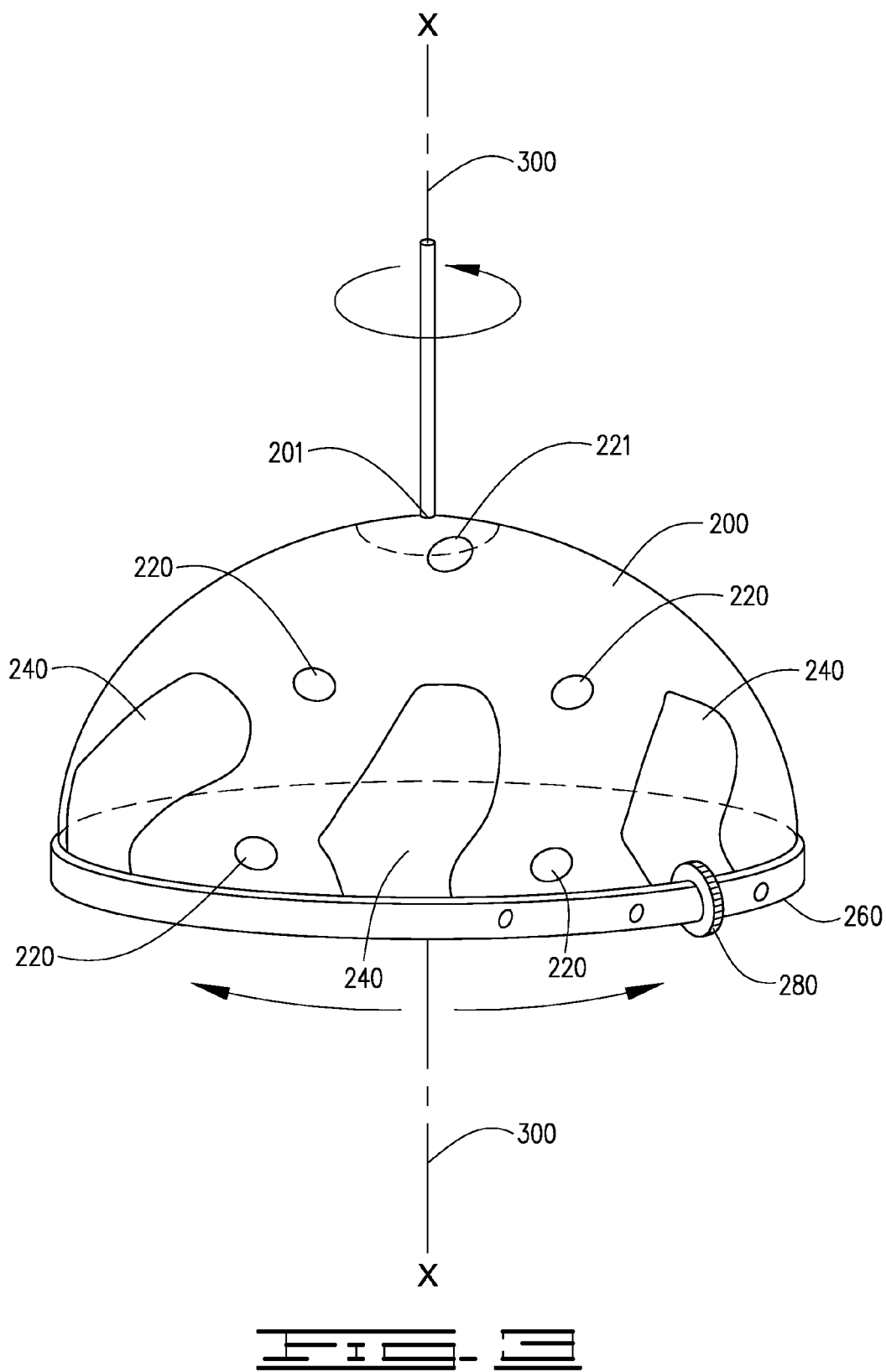
FIG. 3 shows a side view of the cap given in FIG. 2, according to an embodiment of the invention.

Referring now to FIG. 3, an adjustment strap 260 may be provided about the bottom of cap 200, with a knurled adjustment knob 280 to adjust the shape of cap 200 to accommodate various head sizes, in a well-known manner. In another embodiment, the adjustment strap 260 may be overlapped and secured by using a standard hook-and-loop device that is well known to the industry and sometimes marketed under the trademark Velcro®. Other devices for adjusting and securing the strap to accommodate differing head sizes may be used without departing from the scope of the invention.

Cap 200 may be designed for rotation about an axis 300 that passes through the center of rotation 201. Such rotation may be accomplished through any conventional motor means known to the art. The number of diodes 220, the placement of the diodes 220 about the cap 200, the cyclical sequence of rotational movement, and the actuation of the diodes 220 may be design choices that depend upon the areas of the scalp that are intended to be stimulated for hair growth.

In the embodiment shown in FIGS. 2 and 3, five pairs of circumferentially-spaced diodes 220 may be placed so that they flank cutouts 240 in cap 200. An eleventh diode 221 may be located near center of rotation 201. Although only 11 diodes 220, 221 are shown for illustrative purposes, as many as 20 to 30 single diodes 220 may be placed in cap 200 so that they traverse the area of interest on the scalp. Additionally and without departing from the scope of the invention, the site for each diode 220 may comprise a cluster of diodes 220, so that the area traversed by the cluster is broader than the area traversed by a single diode 220. It should also be noted that the spacing of diodes 220, 221, as shown in FIG. 2 and FIG. 3, is not to scale and is understood to be for illustration purposes only.

Referring now to FIG. 4, a polar view is presented of cap 200, showing a schema for describing different patterns for the placement of the diodes 220. Here, a plurality of rays 410, 420, 430, 440, 450 are shown, along which diodes 220 may be positioned according to radii 510, 520, 530, 540, 550. According to the example using five pairs of diodes 220, five rays 410-450 may be postulated, each ray being spaced equidistantly according to angle $\phi$. As a practical matter, each ray 410-450 may fall upon the cap material that remains between two cutouts 240. Two diodes 220 may be positioned at radii 510-550 along a ray 410-450, so that a selected portion of the scalp is traversed. Alternatively, diode 221 may be eliminated. Other spacing patterns may be used according to patterns well known to those skilled in the art.

It is to be understood that the inventive device may accommodate multiple caps 200, each cap being replaceable by another cap 200 having a different light source arrangement therein. The wiring harness 160 may have a standard coupling arrangement for a maximum number of light sources accommodated by the device, so that each light source in the cap 200 is associated with a particular "address" or number. In this way, alternative light source arrangements may be controlled in a known and established manner, according to how the controller 180 is programmed. Furthermore, each cap 200 may be equipped with a standard universal mount well known to the art, e.g. a bayonet arrangement, which permits the cap to be removably attached to the bonnet 120 and motor 210, so that caps 200 may be exchanged as the need arises.

The controller 180 may be adapted to accepted parameters selected by the operator, such as speed of rotation of the cap, angle of rotation, direction (clockwise or counterclockwise), and actuation of the diodes (i.e. points of time at which a particular diode 220 may be turned on or off). A group of such parameters may determine a cyclical sequence that may be stored in the controller 180 for convenience. A cyclical sequence may be developed for different patterns of hair loss, stored within the controller 180, and retrieved as needed, depending upon the patient. For example, in one embodiment, cap 200 may be rotated in one direction intermittently in increments of 36° for periods of 60 sec. each period, so that diode 221 treats the entire of the top of the scalp. If two diodes 221 were provided with a spacing of 180° apart, then a cycle pattern having only 180° of rotation might be required. This rotation may be performed in the same direction for as long as treatment is programmed, or it may be reversed every 180° or 360°, depending on the options that are made available to the operator, which can take many forms, as will readily occur to one skilled in the art.

Alternatively, the controller 180 may be programmed to actuate individual light sources at different power levels and the cap 200 held stationary. Each individual light source may be programmed to illuminate an area of the scalp for a given amount of time and then to cease operation for a given amount of time, with the cyclical sequence thus defined to be repeated for a specified number of repetitions. In this way, areas of the scalp exhibiting severe hair loss may be treated with coherent light at slightly higher power levels simultaneously with other areas that may exhibit only moderate hair loss.

An example of a diode 220 used according to the invention is shown in detail in FIGS. 5A and 5B. The diode 220 shown may be of a standard construction and design, with a window at the top of the diode for emitting coherent light as by a laser. For example, the diode 220 may be a Boston Electronics Model LED34-05, having a window cap that is 3.5 mm in diameter (approx. 0.15 in.). This diode 220 has a peak emission wavelength of 3400 nm (3.4 microns) and a maximum emissive power of 20 µw at 2.5% duty cycle in pulsed mode. However, such diodes of this type may also be operated in continuous mode without departing from the scope of the invention. Diodes of this type may operate at a power level of up to about 100 mw individually, but nominally it is expected that 20 to 30 diodes, each operating at a power level of between about 0 mw to about 15 mw, would be a typical configuration for the invention, with the total wattage expended for all diodes collectively being less than or equal to about 500 mw. The beam divergence/dispersion of this diode may be controlled by means of a lens 222 in the top of the cap 223 surrounding the diode. The lens 222 will exhibit the narrowest dispersion, while a diode cap 223 having no lens will exhibit intermediate dispersion and a capless diode will exhibit the widest dispersion. The divergence/dispersion pattern chosen may be dependent upon the distance between the surface of the scalp and the diode 220, so that sufficient coverage of the scalp area may be achieved.

The light sources of the inventive device described herein for stimulating hair growth may typically be operated at a collective power level of about 500 mw or less. However, there may be certain circumstances where a higher power level is warranted. For example, in the case of cancer patients, the chemotherapy used to treat the cancer will frequently result in hair loss. Such patients have been found to require higher levels of hair follicle stimulation than the normal patient population. These higher levels of stimulation may be provided by power levels that exceed 500 mw for the collective laser light sources but generally not exceeding 1000 mw collectively.

The apparatus thus described may be used to promote hair growth from the scalp of a patient according to a method of the invention. According to the method, one or more of the diodes may be arranged along the inner surface of the cap 200 according to a fixed pattern. A periodic cycle may be programmed into the controller 180 that actuates the cap 200 and diodes 220, which will cause the cap 200 to move in a repeated periodic movement about the scalp. The cap 200 may be arranged so that each diode 220 in the cap 200 is at the same general distance from the scalp. The power supplied to each diode 220 may be from about 0 mw to about 15 mw, so that the total power supplied to all diodes does not exceed 500 mw. The cap 200 may then be allowed to periodically cycle through its programmed course for a fixed length of time. Multiple treatments of this type may be necessary to complete the hair stimulation process.

Thus as can be seen, the invention provides a device and method for the stimulation of hair growth using a multiplicity of diodes operating at longer wavelengths and at lower power than heretofor. It should be understood, of course, that the foregoing relates to exemplary embodiments of the invention and that modifications may be made without departing from the spirit and scope of the invention as set forth in the following claims.

I claim:

1. A method for promoting the hair growth on a scalp of a patient's head, the method comprising the following steps:
    selecting one or more areas on the scalp, wherein each of the one or more areas contain hair follicles for which stimulation is required;
    selecting from a plurality of caps a selected cap having one or more light sources configured thereon in a fixed configuration, the configuration selected to radiate the one or more areas, each light source having a dispersion pattern and emitting a wavelength of coherent light at a specified power level, the wavelength of the coherent light in a range from about 2500 nm to about 10,000 nm:
    attaching the selected cap to a bonnet arranged to hold the cap at the distance from and over the scalp and to rotate the selected cap;
    actuating the one or more light sources according to a periodic cycle; and
    illuminating each of the one or more areas of the scalp with the light sources during the periodic cycle
    wherein each selected area of the scalp is traversed by the dispersion pattern of a light source at least once during the periodic cycle and the traversal of the one or more areas of the scalp during the periodic cycle is accomplished through coordinating selective rotational movement of the cap and actuation of selected light sources in the can.

2. The method according to claim 1, wherein the cap is stationary during the periodic cycle and the light sources are periodically actuated by a controller according to a pattern chosen to illuminate only the one or more selected areas of the scalp.

3. The method according to claim 1, wherein the light sources are periodically actuated by a controller in coordination with bidirectional rotational movement of the cap according to a pattern chosen to illuminate only the one or more selected areas of the scalp.

4. The method according to claim 1, wherein the specified power level of each light source is between 0 mW and 100 mW.

5. The method according to claim 1, wherein the total collective power level of the device is less than about 1000 mW.

6. The method according to claim 1, wherein the specified wavelength of each light source is about 3400 nm.

7. The method according to claim 1, wherein the light source is a diode laser.

8. A device for stimulating hair follicles of a scalp of person through exposure to coherent light, the device comprising:
    a plurality of adjustable caps, each cap formed from a disk of material, the disk having one or more cutouts defining portions of the disk therebetween, the cutouts extending from a circumference of the disk in the general direction of a center of rotation of the disk, each cap formed by folding a circumferential edge of each portion inwardly to adjustably conform to the general shape of the head, each cap positioned a distance away from and over the scalp, each cap having one or more light sources arranged within the portions of the cap to emit a beam of coherent light in a direction of the scalp, each light source emitting coherent light having a wavelength in a range of from about 2500 nm to about 10,000 nm;
    a means for supporting a selected cap from the plurality of caps for movement about the scalp in a cyclical sequence, wherein the movement is selectively rotational and bidirectional; and,
    a means for controlling the movement of the selected cap and the actuation of the light sources.

9. The device according to claim 8, wherein the light source is a diode.

10. The device according to claim 8, wherein the specified power level of each light source is between 0 mW and 100 mW.

11. The device according to claim 8, wherein the total collective power level of the device is less than about 1000 mW.

12. The device according to claim 8, wherein the specified wavelength of each light source is about 3400 nm.

13. The device according to claim 8, wherein the cyclical sequence is stored on a storage device of a controller for subsequent retrieval when required.

14. The device according to claim 8, the selected cap is removably attached to a bonnet for movement in the cyclical sequence.

* * * * *